US00PP22461P2

(12) United States Plant Patent
Clifford et al.

(10) Patent No.: US PP22,461 P2
(45) Date of Patent: Jan. 17, 2012

(54) ***DIANTHUS* PLANT NAMED 'HOPE'**

(50) Latin Name: *Dianthus hybrida*
Varietal Denomination: Hope

(76) Inventors: John K. Clifford, Paw Paw, MI (US); Ken J. Clifford, Paw Paw, MI (US)

( * ) Notice: Subject to any disclaimer, the term of this patent is extended or adjusted under 35 U.S.C. 154(b) by 0 days.

(21) Appl. No.: 12/927,160

(22) Filed: Nov. 9, 2010

(51) Int. Cl.
*A01H 5/00* (2006.01)

(52) U.S. Cl. ..... Plt./272; Plt./282

(58) Field of Classification Search ..... Plt./272, Plt./282
See application file for complete search history.

*Primary Examiner* — Kent L Bell
(74) *Attorney, Agent, or Firm* — Penny J. Aguirre

(57) ABSTRACT

A new cultivar of *Dianthus hybrida*, 'Hope', characterized by its clean, mounded, blue foliage, and its single flowers that are bright fuchsia in color.

2 Drawing Sheets

Botanical classification: *Dianthus hybrida.*
Variety denomination: 'Hope'.

BACKGROUND OF THE INVENTION

The present invention relates to a new and distinct cultivar of *Dianthus* plant, botanically of hybrid origin and known as *Dianthus* 'Hope' and will be referred to hereinafter by its cultivar name, 'Hope'. The new cultivar represents a new cultivar of cheddar pinks, an herbaceous perennial grown for landscape use.

'Hope' was discovered by the Inventors in a container in a nursery in Lewisburg, Tenn. in April of 2007. The new cultivar arose as a chance seedling in a quart container amongst a block of containers of 'Firewitch' (not patented) and 'Frosty Fire'. Although the parentage is unknown, 'Firewitch' and 'Frosty Fire' are likely parents due to the characteristics of the new cultivar and their proximity.

Asexual reproduction of the new cultivar was first accomplished by one of the Inventors using stem cuttings in June of 2007 in Paw Paw, Mich. Using stem cutting and in vitro propagation, the characteristics of this cultivar have been determined to be stable and are reproduced true to type in successive generations.

SUMMARY OF THE INVENTION

The following traits have been repeatedly observed and are determined to be the characteristics of the new cultivar. These attributes in combination distinguish 'Hope' as unique from all other varieties of *Dianthus* known to the Inventors.

1. 'Hope' exhibits single flowers that are bright fuchsia in color.
2. 'Hope' exhibits clean, mounded, blue foliage.

In comparison to its likely parent plant, 'Fire Witch', 'Hope' differs in having cleaner, more blue foliage and flowers that are bright fuchsia rather than pink and in blooming later in the season. In comparison to its likely parent plant, 'Frosty Fire', 'Hope' has similar foliage, however 'Frosty Fire' differs from 'Hope' in having double flowers that are more red in color and in flowering later in the season. 'Hope' can also compared to the *Dianthus* cultivar 'Devon Xera' (U.S. Plant Pat. No. 14,895). 'Hope' has similar foliage to 'Devon Xera', however 'Devon Xera' differs from 'Hope' in having flowers that are crimson red in color with a darker red center eye and in producing less flowers.

BRIEF DESCRIPTION OF THE DRAWING

The accompanying colored photographs illustrate the overall appearance and distinct characteristics of the new *Dianthus*. The photographs in the figures were taken of a plant about six months in age as grown in a garden for two months from a 1-liter container.

Figure 1:
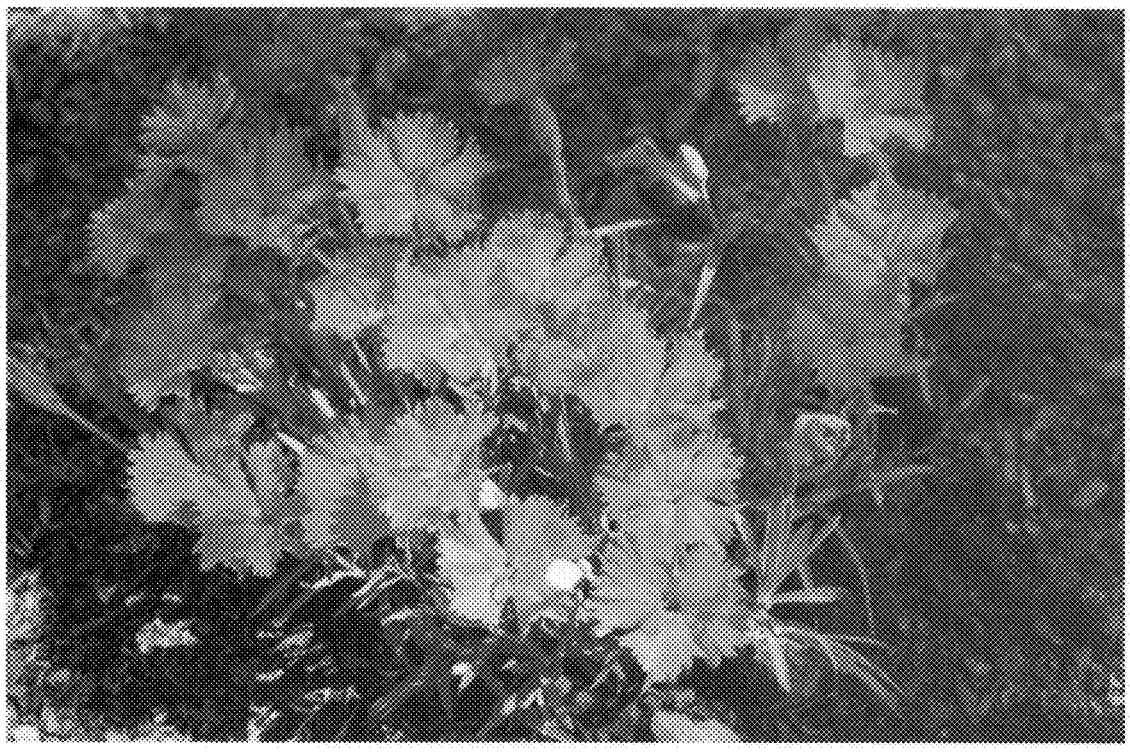
FIG. 1 provides a view of the plant habit of 'Hope' in bloom.
Figure 2:
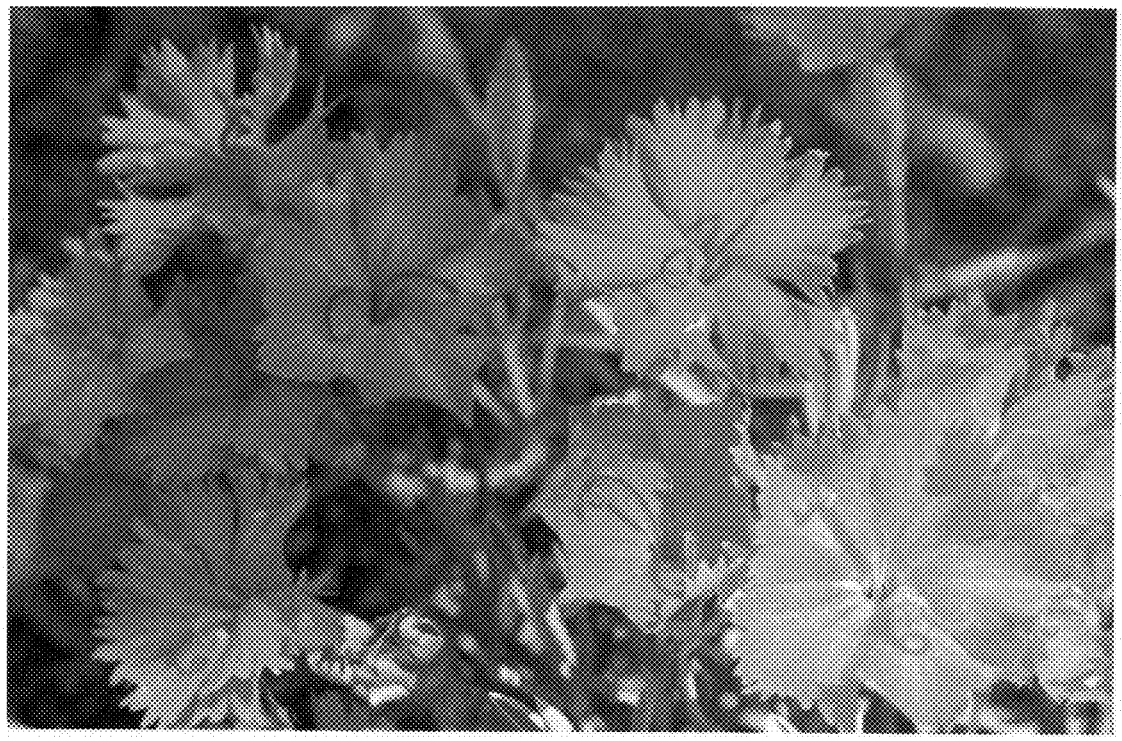
FIG. 2 provides a close-up view of the flowers of 'Hope'.

The colors in the photographs may differ slightly from the color values cited in the detailed botanical description, which accurately describe the colors of the new *Dianthus*.

DETAILED BOTANICAL DESCRIPTION

The following is a detailed description of plants about six months in age as grown in a garden in Michigan for two months from a 1-liter container. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Blooms for about 3 weeks in mid spring in Michigan.

*Plant habit.*—Herbaceous perennial, evergreen, tightly mounded foliage with upright flower scapes.

*Height and spread.*—An average of 15 cm in height and about 20 cm in width.

*Hardiness.*—At least in U.S.D.A. Zones 4 to 9.

*Diseases and pests.*—Has been observed to be more resistant to downy mildew in comparison to other cultivars of *Dianthus* grown by the Inventors.

*Root description.*—Fibrous.

Growth and propagation:

*Propagation.*—Stem cuttings and tissue culture (preferred).

*Growth rate.*—Vigorous.

Stem description:

*Stem strength.*—Strong and held upright.

*Shape.*—Oval, solid swollen at nodes.

*Stem color.*—New growth; 137A with heavy glaucous coating of 189A to 189C, 145B in color near base, woody base (old growth); 165A.

*Stem size.*—Average of 1.2 mm in diameter and 8 cm in length (including peduncle).

*Stem surface.*—Glaucous.

*Branching habit.*—Numerous dense branches emerge in whorls from stout woody stems, about 50 lateral branches per plant.

Foliage description:

*Leaf division.*—Simple.

*Leaf shape.*—Linear.

*Leaf base.*—Blunt, clasping to stem.

*Leaf apex.*—Narrowly acute.

*Leaf margin.*—Entire.

*Leaf venation.*—Linear, not conspicuous, color same as leaf color.

*Leaf attachment.*—Sessile, clasping.

*Leaf arrangement.*—Opposite.

*Leaf surface.*—Glaucous.

*Leaf color.*—Newly emerged and mature upper and lower surface; 137A with heavy glaucous coating of 189B, basal clasping portion N144D.

*Leaf size.*—Average of 2.3 cm in length and 3 mm in width with basal portion clasping leaf about 3 mm width and length.

*Foliage fragrance.*—None.

Flower description:

*Inflorescence type.*—Solitary and pairs of salviform flowers at terminus and upper nodes of lateral branches.

*Lastingness of inflorescence.*—About 4 days.

*Fragrance.*—Mildly sweet.

*Quantity of flowers.*—About 30 flowers per 4 inch container.

*Flower type.*—Salviform.

*Flower size.*—About 3 cm in diameter and 2.5 cm in depth.

*Flower aspect.*—Held upright with petals spreading to nearly horizontal but slightly upward.

*Flower buds.*—About 2 cm in length and 5 mm in width, oblong in shape, color calyx portion 137C with heavy glaucous coating of 189B, petal portion 64B.

*Peduncle.*—An average of 1 cm in length and 1 mm in diameter, 138A in color, glaucous.

*Pedicel.*—Flowers are sessile to peduncle.

*Petals.*—4, limb; obdeltoid in shape, glabrous on upper and lower surface, rounded apex, margins are serrated along apex and sides and entire near base, wavy, about 1.7 cm in width and 1.4 cm in length, color 60B on upper surface and 64B on lower surface, claw; (enclosed in calyx) an average of 1 cm in length and 3 mm in width, color 144D, petals not persistent.

*Calyx.*—Cylindrical in shape, fused sepals with un-fused apex, glaucous surface, average of 1.5 cm in length and 6 mm in width, color 137C with heavy glaucous coating of 189B, persistent and dries to about 164C in color.

*Sepals.*—5, fused, the triangle-shaped tip at apex are un-fused and about 3 mm in length and 3 mm in width.

*Epicalyx.*—Comprised of 4 involucre bracts; oblong to ovate in shape with truncate base and acute apex, about 6 to 8 mm in length and 3 mm in width, color 137C with heavy glaucous coating of 189B, glaucous surface.

Reproductive organs:

*Gynoecium.*—Pistil; 2, about 2 cm in length at maturity, styles; N155C in color, crystalline in appearance, about 1.9 cm in length, stigma; extends down surface of style, about 1 cm in length, pilose, color N79B, curled at apex, ovary; superior, oblong in shape, 8 mm in length and 3.5 mm in width, 144A in color.

*Androecium.*—Stamens; 10, fused at base in ring around base of ovary, about 5 mm in length, filament; 145D in color, about 4 mm in length, crystalline in appearance, anthers; 165D in color, dorsifixed, oblong in shape, about 1 mm in length and 0.5 mm in width, appear papery, pollen; not discernable.

*Fruit and seed.*—Fruit; a capsule formed by calyx, development of seeds was not observed.

It is claimed:

1. A new and distinct cultivar of *Dianthus* plant named 'Hope' as herein illustrated and described.

* * * * *